(12) United States Patent
Spurr et al.

(10) Patent No.: US 6,384,214 B1
(45) Date of Patent: May 7, 2002

(54) PROCESS FOR PRODUCING CEPHALOSPORIN DERIVATIVES

(75) Inventors: Paul Spurr, Riehen (CH); Georg Trickes, Lörrach (DE)

(73) Assignee: Basilea Pharmaceutica AG, Binningen (CH)

( * ) Notice: Subject to any disclaimer, the term of this patent is extended or adjusted under 35 U.S.C. 154(b) by 0 days.

(21) Appl. No.: 09/610,647

(22) Filed: Jun. 29, 2000

(30) Foreign Application Priority Data

Jul. 5, 1999 (EP) .............................. 99112911

(51) Int. Cl.$^7$ ............................ C07D 501/24
(52) U.S. Cl. .................................... 540/222
(58) Field of Search ......................... 540/222

(56) References Cited

U.S. PATENT DOCUMENTS

| | | | |
|---|---|---|---|
| 5,523,400 A | 6/1996 | Wei et al. | 514/202 |
| 5,856,474 A | 1/1999 | Ascher et al. | 540/222 |

FOREIGN PATENT DOCUMENTS

| | | |
|---|---|---|
| EP | 620 225 | 10/1994 |
| EP | 761673 | 3/1997 |
| EP | 831093 | 3/1998 |
| EP | 849 269 | 6/1998 |
| WO | WO 00/32605 | * 8/2000 |

* cited by examiner

*Primary Examiner*—Mark L. Berch
(74) *Attorney, Agent, or Firm*—George W. Johnston; Patricia S. Rocha-Tramaloni; Eileen M. Ebel

(57) ABSTRACT

The present invention is concerned with a novel process for the manufacture of cephalosporin derivatives of the formula

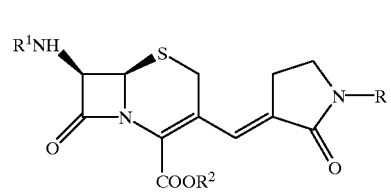

I by converting a phosphonium salt into the corresponding ylide and reacting same with an aldehyde wherein $R^1$ and $R^2$ are as above.

18 Claims, No Drawings

PROCESS FOR PRODUCING CEPHALOSPORIN DERIVATIVES

BACKGROUND OF THE INVENTION

Certain Δ2 double bond cephalosporin derivatives are known to be valuable intermediates for the manufacture of pharmacologically useful cephalosporins as described in EP-A-620 225 and in EP-A-849 269. In a known process these cephalosporin derivatives are prepared from a phosphonium salt and a Δ2 double bond aldehyde in the presence of a base such as 1,2-butyleneoxide or triethylamine in an inert solvent to yield the Δ3-isomer of the cephalosporin derivative. This is due to the fact that the Δ2 double bond is very sensitive towards bases in solution and readily migrates to the 3-position. The formation of the Δ3-reaction product necessitates the correction of the position of the double bond to the desired 2-position by a two-step redox sequence. In the known process this is effected by oxidation to the corresponding sulfoxide with hydrogen peroxide or a peracid and deoxygenation thereof with phosphorus tribromide. These reagents, in particular the latter, are corrosive and dangerous to use on a large scale.

Efforts to obtain these cephalosporin derivatives directly via reaction of the phosphonium salt and Δ2 aldehyde are hampered by the sensitivity of Δ2 cephalosporins to bases in solution. Therefore, it would be useful to develop a process in which this isomerization does not occur.

SUMMARY OF THE INVENTION

The present invention is concerned with a process for producing compounds of formula

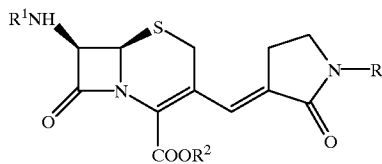

I wherein
$R^1$ is an amino protecting group,
$R^2$ is a carboxy protecting group, and
R is hydrogen, lower alkyl, lower alkoxy, cycloalkyl, cycloalkenyl, cycloalkyl-lower alkyl, lower alkenyl, lower alkynyl, aryl, aryl-lower alkyl, heterocyclyl or heterocyclyl-lower alkyl; the lower alkyl, cycloalkyl, lower alkenyl, cycloalkenyl, lower alkynyl, aryl-lower alkyl, aryl and the heterocyclyl moieties being unsubstituted or substituted with at least one group selected from carboxy, amino, aminoethyl, carbamoyl, nitro, cyano, lower alkyl, lower alkoxy, hydroxy, halogen and trifluoromethyl which comprises treating a phosphonium salt of formula

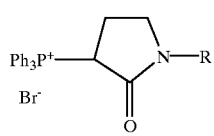

II in a toluene reaction mixture with a base, said base being present in a molar amount which is less than the molar amount of said phosphonium salt, to form an ylide of formula

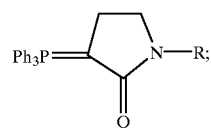

III coupling the ylide of formula III with an aldehyde of formula

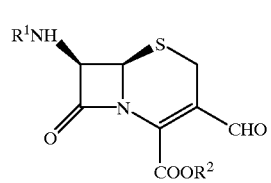

IV by adding to the reaction mixture a solution of the aldehyde of formula IV in a polar solvent at a temperature of from about −80° C. to about 0° C.; to produce the compound of formula I.

Preferably, the process involves the manufacture of cephalosporin derivatives of the formula

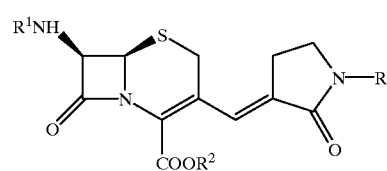

I wherein
$R^1$ is an amino protecting group,
$R^2$ is a carboxy protecting group, and
R is hydrogen, lower alkyl, lower alkoxy, cycloalkyl, cycloalkenyl, cycloalkyl-lower alkyl, lower alkenyl, lower alkynyl, aryl, aryl-lower alkyl, heterocyclyl or heterocyclyl-lower alkyl; the lower alkyl, cycloalkyl, lower alkenyl, cycloalkenyl, lower alkynyl, aryl-lower alkyl, aryl and the heterocyclyl moieties being unsubstituted or substituted with at least one group selected from carboxy, amino, aminoethyl, carbamoyl, nitro, cyano, lower alkyl, lower alkoxy, hydroxy, halogen, trifluoromethyl and allyloxycarbonyl which is substituted on a ring nitrogen of pyrrolidinyl.

The process is characterized in that it comprises converting a phosphonium salt of the formula

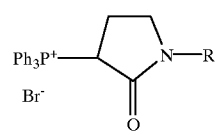

II wherein R is as above and Ph represents phenyl,
in toluene by treatment with a base into the corresponding ylide of the formula

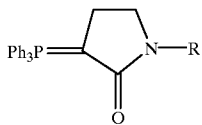

III wherein R and Ph are as above,
and reacting same with a solution in a polar solvent of an aldehyde of the formula

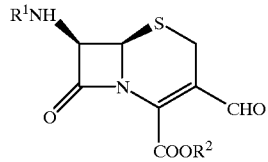

IV wherein $R^1$ and $R^2$ are as above,
at a temperature of from about −80° C. to about 0° C., the phosphonium salt II, base and aldehyde IV being employed in a molar ratio of about 1.15:1.1:1.0 to 1.3:1.25:1.0. The molar amount of base is less than that of the phosphonium salt.

DETAILED DESCRIPTION OF THE INVENTION

Accordingly, this invention is directed to a method of producing a compound of formula

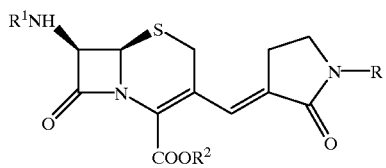

I wherein
$R^1$ is an amino protecting group,
$R^2$ is a carboxy protecting group, and
$R^2$ is hydrogen, lower alkyl, lower alkoxy, cycloalkyl, cycloalkenyl, cycloalkyl-lower alkyl, lower alkenyl, lower alkynyl, aryl, aryl-lower alkyl, heterocyclyl or heterocyclyl-lower alkyl; the lower alkyl, cycloalkyl, lower alkenyl, cycloalkenyl, lower alkynyl, aryl-lower alkyl, aryl and the heterocyclyl moieties being unsubstituted or substituted with at least one group selected from carboxy, amino, aminoethyl, carbamoyl, nitro, cyano, lower alkyl, lower alkoxy, hydroxy, halogen, trifluoromethyl and allyloxycarbonyl which is substituted on a ring nitrogen of pyrrolidinyl
which comprises treating a phosphonium salt of formula

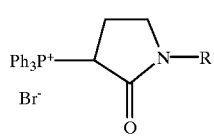

II in a toluene reaction mixture with a base, said base being present in a molar amount which is less than the molar amount of said phosphonium salt, to to form an ylide of formula

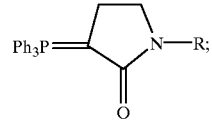

III coupling the ylide of formula III to the aldehyde of formula

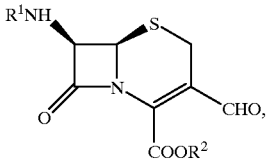

IV by adding to the reaction mixture a solution of the aldehyde of formula IV in a polar solvent at a temperature of from about −80° C. to about 0° C. (preferably about −80° C. to about −60° C., most preferably about −70° C.); wherein said base, ylide, and aldehyde are present in the reaction mixture during the formation of the compound of formula I in molar ratio of about 1.15:1.1:1.0 to 1.3:1.25:1.0, and preferably about 1.2:1.15:1.0, to produce the compound of formula I. It is important that the molar amount of base is less than that of the phosphonium salt.

A preferred polar solvent is tetrahydrofuran. Preferred bases include aqueous sodium hydroxide and potassium tert.butoxide in tetrahydrofuran.

When the base is potassium tert.butoxide in tetrahydrofuran, it is preferable that the toluene reaction mixture further comprises methylene chloride and the polar solvent is tetrahydrofuran, in the preferred weight ratio of about 2:1:1 to 5:2:1. Under these conditions, a preferred R is N-substituted 3-pyrrolidinyl, especially N-allyloxycarbonyl-3-pyrrolidinyl.

Preferred aldehydes of formula IV are diphenylmethyl (6R,7R)-7-(1-tert-butoxyformamido)-3-formyl-8-oxo-5-thia-1-azabicyclo[4.2.0]oct-2-ene-2-carboxylate and 4-methoxybenzyl (6R,7R)-7-phenylacetylamino-3-formyl-8-oxo-5-thia-1-azabicyclo[4.2.0]oct-2-ene-2-carboxylate.

It is preferred that R is selected from substituted lower alkyl (such as 2,2,2-trifluoroethyl), or unsubstituted or substituted cycloalkyl (such as cyclopropyl or cyclopropylmethyl). Heterocyclyl is also a preferred R, such as 5 or 6-membered rings containing one or two heteroatoms (preferably nitrogen), especially substituted heterocyclyl such as N-substituted 3-pyrrolidinyl (such as N-allyloxycarbonyl-3-pyrrolidinyl).

As used herein, the terms "lower alkyl" and "optionally substituted lower alkyl" refer to both straight and branched chain saturated hydrocarbon groups having 1 to 8, preferably 1 to 4 carbon atoms, for example, methyl, ethyl, n-propyl, isopropyl, tertiary butyl and the like. The lower alkyl groups can be unsubstituted or substituted by at least one substituent such as halogen. Preferred substituents are fluoro, examples of substituted lower alkyl are trifluoromethyl, 2,2,2-trifluoroethyl, perfluorohexyl and the like.

By term "lower alkoxy" is meant an ether group wherein alkyl is as defined above. Examples are methoxy, ethoxy, propyloxy and the like.

By the term "cycloalkyl" is meant a 3–7 membered saturated carbocyclic ring, e.g. cyclopropyl, cyclobutyl, cyclopentyl, cyclohexyl and the like. "Cycloalkyl-lower alkyl" is an alkyl group as defined above with an attached cycloalkyl ring. Preferred cycloalkyl-lower alkyls are for example cyclopropylmethyl and cyclopropylethyl. By the term "cycloalkenyl" is meant a 4–7 membered carbocyclic ring having at least one olefinic double bond, e.g. cyclopentenyl.

As used herein, "lower alkenyl" refers to an unsubstituted or substituted hydrocarbon chain radical having from 2 to 8 carbon atoms, preferably from 2 to 4 carbon atoms, and having at least one olefinic double bond, e.g. vinyl, allyl, and the like.

As used herein, "lower alkynyl" refers to an unsubstituted or substituted hydrocarbon chain radical having from 2 to 8 carbon atoms, preferably 2 to 4 carbon atoms, and having at least one triple bond, e.g. ethynyl, 1-propynyl, 2-propynyl.

The term "halogen" used herein refers to chlorine or chloro; bromine or bromo; iodine or iodo; and fluorine or fluoro.

By the term "aryl" is meant a radical derived from an aromatic hydrocarbon by the elimination of one atom of hydrogen which can be substituted or unsubstituted. The aromatic hydrocarbon can be mononuclear or polynuclear. Examples of aryl radicals of the mononuclear type include phenyl, tolyl, xylyl, mesityl, cumenyl and the like. Examples of aryl radicals of the polynuclear type include naphthyl, anthryl, phenanthryl and the like. The aryl group can have at least one substituent selected from halogen, hydroxy, cyano, carboxy, carbamoyl, nitro, amino, aminomethyl, lower alkyl, lower alkoxy and trifluoromethyl. Examples include 2-fluorophenyl, 3-nitrophenyl, 4-nitrophenyl, 4-methoxyphenyl, 4-hydroxyphenyl and the like. The abbreviation "Ph" such as used in formula II stand for phenyl.

By the term "aryl-lower alkyl" is meant a lower alkyl group containing an aryl group as defined above, for example benzyl or benzhydryl.

As used herein, "heterocyclyl" refers to an unsaturated or saturated, unsubstituted or substituted 5-, 6-, or 7-membered heterocyclic ring containing at least one hetero atom selected from the group consisting of oxygen, nitrogen and sulfur. Exemplary heterocyclic rings include, but are not limited to, e.g., the following groups: pyrrolidinyl, pyridinyl, pyridiniumyl, pyrazinyl, piperidyl, piperidino, N-oxido-pyridyl, pyrimidyl, piperazinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, azetidinyl, furyl, hexamethyleneiminyl, oxepanyl, 1H-azepinyl, thiophenyl, tetrahydro-thiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, tetrahydrothienyl, and the like. Preferred heterocyclic rings are pyridinyl, pyridiniumyl, piperidyl, pyrrolidinyl (particularly 3-pyrrolidinyl) and azetidinyl. Substituents for the heterocyclic ring include lower-alkyl, lower alkoxy, halogen, trifluoro-methyl, trichloroethyl, amino, mercapto, hydroxy, carboxy and carbamoyl. Preferred examples of substituted heterocyclic rings include 5-methyl-isoxazol-3-yl, N-methyl-pyridinium-2-yl, N-methyl-pyrrolidinyl, 1-methyl-tetrazolyl, N-allyloxycarbonyl-3-pyrrolidinyl, and methyl-pyridinium-2-yl.

The heterocyclic ring can also be substituted by an optionally substituted phenyl ring such as 2,6-dichlorophenyl. Preferred is 2,6-dichlorophenyl-5-methyl-isoxazolyl. A further substituent of the heterocyclic ring is oxo, such as in 2-oxo-oxazolidin-3-yl and 1,1-dioxo-tetrahydrothien-3-yl. The heterocyclic ring can also be fused together with a benzene ring.

As used herein, "heterocyclyl-lower alkyl" refers to a lower alkyl group containing a heterocyclic group as defined above, e.g. tetrazolyl-methyl, tetrahydrofuranyl-methyl, thiophenyl-methyl or benzimidazolyl-methyl.

Amino protecting groups are groups which can be cleaved off under known conditions to yield the free amino group. Possible amino-protecting groups $R^1$ are those employed in peptide chemistry, such as an alkoxycarbonyl group, e.g., t-butoxycarbonyl, etc., a substituted alkoxycarbonyl group, e.g., trichloroethoxycarbonyl etc., an arylalkanoyl group, e.g. phenylacetyl, a heteroarylalkanoyl group, e.g. 2-thienyl-acetyl or 2-furyl-acetyl; an optionally substituted aralkyloxycarbonyl group, e.g., p-nitrobenzyloxycarbonyl or benzyloxycarbonyl, an aralkyl group such as trityl or benzhydryl or a halogen-alkanoyl group such as chloroacetyl, bromoacetyl, iodoacetyl or trifluoroacetyl. Preferred amino-protecting groups are t-butoxycarbonyl (t-BOC), phenylacetyl and trityl.

Carboxy protecting groups are groups which can be cleaved off under known conditions to yield the carboxy group. As carboxy protecting groups $R^2$ one may utilize an ester form which can be easily converted into a free carboxyl group under mild conditions, the ester protecting group being exemplified by, for example, t-butyl, p-nitrobenzyl, p-methoxybenzyl, allyl or benzhydryl.

Efforts to obtain compounds I directly via reaction of compounds II and IV are hampered by the sensitivity of Δ2 cephalosporins, such as compounds I and IV, to bases in solution. However, it has been found that the Δ2-aldehyde IV as well as the reaction product I dissolved in toluene are stable and do not isomerize in the presence of the ylide III formed from the phosphonium salt II as long as the molar ratio of the base is not in excess of that of the starting phosphonium salt II. Apparently the basicity of the ylide III, which is present in slight excess, is too weak to induce the isomerization of compounds IV and I in toluene.

In carrying out the process in accordance to the invention, the phosphonium salt is preferably dispersed in toluene, or a mixture of toluene and methylene chloride, and submitted to treatment with a base, e.g. with aqueous alkali, e.g. 0.1N–1N aqueous NaOH or KOH or, in the absence of water, with sodium or potassium tert.-butylate in a polar organic solvent such as tetrahydrofuran or dioxane, preferably in tetrahydrofuran. In adding the alkali tert.-butylate in tetrahydrofuran the deprotonation step in forming the ylide III is accelerated and the advantage is reached, that addition of a solid to the system is avoided, which is of advantage due to the low reaction temperature. Also, the system can in this way advantageously be precooled to reaction temperature prior to adding the alkali tert.butylate in tetrahydrofuran.

The resulting ylide III solution/suspension, if not already cooled to reaction temperature as above, is now brought thereto, i.e. to between about 0° C. and about −80° C., preferably to about −60° C. to about −80° C., most preferably to about −70° C., and brought to reaction with the aldehyde IV in solution in a polar organic solvent such as tetrahydrofuran or dioxane, preferably tetrahydrofuran. The molar ratio of the reactants (phosphonium salt II:alkali:aldehyde IV as given above) avoids the undesired Δ2/Δ3 migration of the double bond of the resulting end product I, particularly when the molar ratio is about 1.2:1.15:1.0.

The reaction time varies between about ½ hour and 2 hours.

In preferred embodiments of the process of the invention diphenylmethyl (6R,7R)-7-(1-tert-butoxyformamido)-3-formyl-8-oxo-5-thia-1-azabicyclo[4.2.0]oct-2-ene-2-carboxylate or 4-methoxybenzyl (6R,7R)-7-phenylacetylamino-3-formyl-8-oxo-5-thia-1-azabicyclo[4.2.0]oct-2-ene-2-carboxylate is used as starting aldehyde of formula IV.

Preferred starting phosphonium salts of formula II are such wherein R is 2,2,2-trifluoroethyl, cyclopropyl, cyclopropylmethyl or N-substituted 3-pyrrolidinyl, such as N-allyloxycarbonyl-3-pyrrolidinyl. The allyloxycarbonyl group is a protecting group which is subsequently split off to yield end products of formula V below, in which R is 3-pyrrolidinyl.

Where R is N-substituted 3-pyrrolidinyl, such as N-allyloxycarbonyl-3-pyrrolidinyl, the process is preferably carried out in non-aqueous phase in a mixture of toluene, methylene chloride and tetrahydrofuran, preferably in a weight ratio of between about 2:1:1 and 5:2:1. In a preferred embodiment the phosphonium salt II is dissolved in methylene chloride, toluene is added, followed by potassium tert.-butylate in tetrahydrofuran solution and finally by aldehyde IV in tetrahydrofuran and reacted for ½–2 hours at about –80° C. to –60° C.

The resulting toluene reaction mixture contains crude reaction product of formula I. In order to avoid migration of the Δ2 double bond to the 3-position, work-up is effected in aqueous acid, e.g. by adding 0.1–1N aqueous HCl or citric acid. By extraction of the so acidified reaction mixture in usual manner, recovery of the toluene solution and evaporation thereof a crude product of formula I is obtained, which can be used for further reactions to pharmacologically useful cephalosporins. If desired, the crude product can be further purified in known manner e.g. by flash chromatography on silica gel with a suitable solvent or solvent mixture, e.g. methylene chloride, toluene:ethyl acetate or n-hexane:ethyl acetate.

The process of the present invention offers easier access to pharmacologically useful cephalosporins e.g. of the formula

V

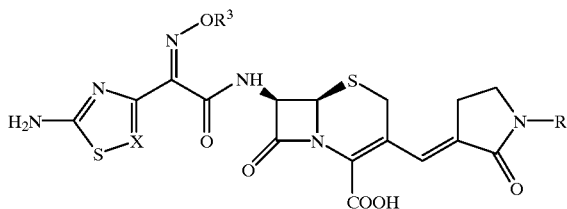

wherein
R is as above,
X is —CH— or nitrogen, and
$R^3$ is hydrogen, optionally substituted lower alkyl, cycloalkyl, benzyl, trityl, acetyl or tetrahydropyranyl, and their pharmaceutically acceptable salts and in vivo cleavable esters.

The process for arriving at compounds V is thus shortened, offers higher yields and avoids problematic reagents. Compounds V can be obtained from compounds I according to directions given in EP-A 620 225 and in EP-A-849 269.

In a preferred embodiment of compounds V R is 2,2,2-trifluoroethyl, cyclopropyl, cyclopropylmethyl or 3-pyrrolidinyl, X is —CH— and N and $R^3$ is hydrogen.

The following examples illustrate the invention in more detail.

EXAMPLE 1

Under argon 85.5 g of (R,S) (1-cyclopropylmethyl-2-oxo-pyrrolidin-3-yl)-triphenyl-phosphonium bromide are dispersed in 1 l of toluene. To the suspension a solution of 19.5 g of potassium tert.-butylate in 450 ml of tetrahydrofuran (THF) is added dropwise within 40 min. The white suspension is colored yellow and a slight exothermic reaction ensues (the temperature rises from 22 to 25° C.).

The suspension is stirred 10 min at room temperature and subsequently cooled to –10° C. A solution of 77.0 g of diphenylmethyl (6R,7R)-7-(1-tert-butoxyformamido)-3-formyl-8-oxo-5-thia-1-azabicyclo[4.2.0]oct-2-ene-2-carboxylate in 300 ml of THF is slowly added dropwise within 1.15 hours. After stirring for 20 min at –10° C., 170 ml of 1 N aqueous hydrochloric acid and 500 ml of water are added, the mixture taken to room temperature and stirred for 20 min at room temperature; two clear phases are obtained. The mixture is extracted twice with each 500 ml of toluene and the organic phases washed with each 350 ml of 5% aqueous sodium bicarbonate solution and 300 ml of water. The toluene phases are dried and evaporated to dryness. 159.2 g of crude reaction product are obtained as a dark red mass. This is purified by dissolving same in 1.2 l of methylene chloride, 300 g of silica gel (Merck 60; 0.040–0.063 mm) are added, the mixture is stirred 10 min, filtered and washed portionwise with about 1 liter of methylene chloride. The filtrate is evaporated to dryness and dried. 95 g of yellow-brown crude product is obtained, which is dissolved in 400 ml of n-hexane:ethyl acetate 3:2 and 40 ml of methylene chloride. The solution is flash-chromatographed (200–300 ml fractions) on 1.3 kg of silica gel (Merck 60; 0.040–0.063 mm) with n-hexane: ethyl acetate 3:2 (23 l) as eluent. The fractions (about 10 l) are evaporated to crystallization, filtered and washed with n-hexane; 35.3 g snow white crystals of (E)-(6R,7R)-7-tert-butoxycarbonylamino-3-(1-cyclopropylmethyl-2-oxo-pyrrolidin-3-ylidenemethyl)-8-oxo-5-thia-1-aza-bicyclo[4.2.0]oct-2-ene-2-carboxylic acid benzhydryl ester are obtained (39% yield) melting at 175–180° C.

From the mother liquor a second crop of product is obtained:

10.3 g white/yellow crystals (11.3% yield) melting at 175–180° C.

EXAMPLE 2

Under argon 1.40 g of (R,S)-(1-cyclopropyl-2-oxo-3-pyrrolidinyl)triphenyl-phosphonium bromide are dispersed in 20 ml of toluene. At room temperature a solution of 0.33 g of potassium tert.-butylate in 8 ml of THF is added dropwise within 20 min. An exothermic reaction ensues (the temperature rises from 22 to 25° C.) and the suspension is colored yellow and stirred for 30 min at room temperature, cooled to –10° C., whereafter a solution of 1.34 g of diphenylmethyl (6R,7R)-7-(1-tert-butoxyformamido)-3-formyl-8-oxo-5-thia-1-azabicyclo[4.2.0]oct-2-ene-2-carboxylate in 4 ml of THF is added dropwise within 20 min. After the addition of a mixture of 5 ml of 1N aqueous hydrochloric acid and 10 ml of water stirring is maintained for 10 min at room temperature. The aqueous phase is separated and washed with two portions of 25 ml of toluene, the collected organic phases washed with about 20 ml of 5% aqueous sodium bicarbonate solution and subsequently with 20 ml of water. The toluene phases are combined, dried over 15 g of magnesium sulphate and evaporated to dryness. 2.16 g of red-orange crude [6R-[3(E)-6R,7R]]-3-[(1-cyclopropyl-2oxo-3-pyrrolidinylidene]methyl]-7-[[(1,1-dimethylethoxy)carbonyl]amino]-8-oxo-5-thia-1-azabi-cyclo[4.2.0]oct-2-ene-2-carboxylic acid diphenylmethyl ester are obtained, which are dissolved in 20 ml of toluene/ethyl acetate 3:2 and flash-chromatographed (15 ml fractions) on 30 g of silica gel (Merck 60; 0.040–0.063 mm) with about 500 ml of toluene/ethyl acetate 3:2 as eluent.

There is obtained

Fr 1 0.07 g as orange oil

Fr 2 0.60 g as light yellow crystals

Fr 3 0.46 g as orange crystals

Total: 1.13 g, corresponding to 75% yield.

EXAMPLE 3

In an argon atmosphere 11.2 g of (R,S)-(1-cyclopropyl-2-oxo-3-pyrrolidinyl)-triphenylphosphonium bromide are dissolved in 60 ml of toluene and 30 ml of water and cooled to 0° C. (crystallizes again). 24 ml of 1N aqueous sodium hydroxide are added dropwise within 20 min; the toluene phase colors yellow and the aqueous phase white (suspension). After stirring for 10 min at 0° C. the toluene phase is cooled to −10° C. and the aqueous phase extracted with 20 ml of toluene which is added to the toluene phase. A solution of 10.4 g of diphenylmethyl (6R,7R)-7-(1-tert-butoxyformamido)-3-formyl-8-oxo-5-thia-1-azabicyclo[4.2.0]oct-2-ene-2-carboxylate in 35 ml of THF is added dropwise within 1 hour; the resulting brown suspension is stirred for 10 min. After stirring at 0° C. for 45 min, a mixture of 25 ml of 1N aqueous hydrochloric acid and 25 ml of water is added and stirring is continued for 10 min without cooling (room temperature) to yield two clear phases; the toluene phase is red and the water phase pale yellow. After separation of the phases the water phase is extracted twice with each 50 ml of toluene, the combined organic phases are washed with 50 ml of 5% aqueous sodium bicarbonate solution and afterwards with 50 ml of water. The combined toluene phases are dried over 25 g of magnesium sulphate and evaporated. 20.47 g of red-orange crude product result, which are dissolved in 50 ml of toluene/ethyl acetate (30 min) and subsequently flash-chromatographed (50–75 ml fractions) on 200 g of silica gel (Merck 60; 0.040–0.063 mm) with 4 l of toluene:ethyl acetate 4:1 as eluent.

Yield: 9.5 g [6R-[3(E)-6R,7R]]-3-[(1-cyclopropyl-2-oxo-3-pyrrolidinylidene)methyl]-7-[[(1,1-dimethylethoxy)carbonyl]amino]-8-oxo-5-thia-1-azabicyclo[4.2.0]oct-2-ene-2-carboxylic acid diphenylmethyl ester as yellow crystals (49% based on converted aldehyde).

EXAMPLE 4

Under argon 11.4 g of (R,S)-[2-oxo-1-(2,2,2-trifluoroethyl)-3-pyrrolidinyl]-triphenylphosphonium bromide are dispersed in 100 ml of toluene and 80 ml of water. The resulting three-phase mixture is stirred at room temperature, and 22.4 ml of 1N aqueous sodium hydroxide are added within 30 min. The toluene phase is colored yellow, the water phase colorless and a slight emulsion is obtained.

After 30 min the phases are separated and the aqueous phase extracted with 20 ml of toluene, the organic extracts are washed with 30 ml of 5% aqueous sodium acetate solution and afterwards with 30 ml of water. The combined toluene phases are cooled to −10° C., and 10.0 g of diphenylmethyl (6R,7R)-7-(1-tert-butoxyformamido)-3-formyl-8-oxo-5-thia-1-azabicyclo[4.2.0]oct-2-ene-2-carboxylate in 40 ml of THF are added dropwise within 30 min; the yellow solution is stirred for 20 min at −10° C. Subsequently, a mixture of 40 ml of 1N aqueous hydrochloric acid and 40 ml of water is added and stirring continued for 15 min. The phases are separated, the aqueous phase extracted with two portions of 60 ml of toluene each, the organic phases are washed with 50 ml of 5% aqueous sodium bicarbonate solution and subsequently with 50 ml of water. The combined toluene phases are dried over 85 g of magnesium sulphate and evaporated to dryness. 22.28 g of dark yellow crude reaction product is obtained, which is dissolved in 40 ml of n-hexane:ethyl acetate 3:2 and 3 ml of methylene chloride (30 min). The solution is flash-chromatographed on 100 g of silica gel (Merck 60; 0.040–0.063 mm; diameter 3 cm, length 30 cm) and filtered. As eluent is used 1 l of n-hexane:ethyl acetate 3:2; 50 ml fractions are collected. One obtains 11.55 g of yellow-orange product (yield 96%).

This product is crystallized by dissolving in 20 ml of ethyl acetate at 75° C. and 25 ml of n-hexane are added dropwise in the course of 15 min; the solution is slowly cooled to 60° C., seeded with purified crystals at 60° C., diluted with 25 ml of n-hexane and stirred for 12 hours at room temperature, filtered, washed and dried to yield 8.79 g of [6R-[3(E),6R,7R]]-7-[[(1,1-dimethylethoxy)carbonyl]amino]-8-oxo-3-[[2-oxo-(2,2,2-trifluoroethyl)-3-pyrrolidinylidene]methyl]-5-thia-1-azabicyclo[4.2.0]oct-2-ene-2-carboxylic acid diphenylmethyl ester as white crystals (73% yield), melting at 179–181° C.

EXAMPLE 5

Under argon 27.6 g of (R,S)-[2-oxo-1-(2,2,2-trifluoroethyl)-3-pyrrolidinyl]-triphenyl-phosphonium bromide are dispersed in 240 ml of toluene and 180 ml of water at room temperature. 54.3 ml of 1N aqueous sodium hydroxide solution are added dropwise over 20 min. After 30 min the phases are separated and the water phase extracted three times with each 150 ml of toluene. The toluene phase is extracted three times which each 150 ml of water. The combined toluene phases are cooled to −10° C. and 22 g of 4-methoxybenzyl-(6R,7R)-7-phenylacetylamino-3-formyl-8-oxo-5-thia-1-azabicyclo[4.2.0]oct-2-ene-2-carboxylate in 100 ml of THF added dropwise during 1 hour. After further stirring for 10 min the phases are separated, and the aqueous phase is extracted twice with each 150 ml of toluene. Each toluene phase is washed three times with each 150 ml of water. The combined organic phases are dried over sodium sulphate, filtered and evaporated to about 200 ml. The crystallized product is filtered off and washed with ice-cold toluene. 18.73 g of [6R-[3(E),6R,7R]]-7-phenylacetylamino-8-oxo-3-[[2-oxo-(2,2,2-trifluoroethyl)-3-pyrrolidinylidene]methyl]-5-thia-1azabicyclo[4.2.0]oct-2-ene-2-carboxylic acid 4-methoxybenzyl ester are obtained as yellowish-beige crystals (56% yield) melting at 177° C.

EXAMPLE 6

Under argon 753 mg (1.3 mmol) of a mixture of (1R,3'R) and (1S,3'R)-(1-allyloxy-carbonyl-2-oxo-[1,3']bipyrrolidinyl-3-yl)-triphenyl-phosphonium bromide (1:1) are dissolved in 20 ml of methylene chloride, 3.0 g of sodium sulphate are added, and the mixture is stirred 10 min at room temperature. The sodium sulphate is filtered off and the solution evaporated completely. The residue is dissolved in a mixture of 2 ml of methylene chloride and 5 ml of toluene and the solution cooled to −70° C. 35 mg (1.2 mmol)

of potassium tert.-butylate in 2 ml of THF are added within 5 min at this temperature. The mixture is stirred for another 5 min, and then a solution of diphenylmethyl (6R,7R)-7-(1-tert-butoxyformamido)-3-formyl-8-oxo-5-thia-1-azabicyclo [4.2.0]oct-2-ene-2-carboxylate in 2 ml of THF is added dropwise within 15 min. The reaction mixture is stirred for 2½ hours at −70° C. and subsequently slowly brought to −10° C. After 1 hour at −10° C. a solution of 300 mg of citric acid in 3 ml of water and 4 ml of ethyl acetate are added slowly and the reaction mixture brought to room temperature. Extraction of the resulting two-phase solution is carried out, in that after equilibration the aqueous phase is extracted again with 10 ml of ethyl acetate and the two organic phases extracted with each 3 ml of saturated aqueous sodium bicarbonate solution followed by each 3 ml of saturated aqueous sodium chloride solution. The organic phases are combined, dried and evaporated to yield 1.34 g of an orange-brown residue. This is filtered through a column of 27 g of finely powdered $SiO_2$, using as eluent ethyl acetate:n-hexane 2:1 (5 fractions of each 15 ml discarded) then ethyl acetate only (fractions 6–11 of each 15 ml discarded), fractions 12–20 of each 15 ml yield, after evaporation, 640 mg of (E)-(6R,7R)-3-[(R)-1'-allyloxycarbonyl-2-oxo-[1,3']bipyrrolidinyl-3-ylidenemethyl]-7-tert-butoxycarbonyl-amino-8-oxo-5-thia-1-azabicyclo[4.2.0]oct-2-ene-2-carboxylic acid benzhydryl ester as a yellow resinous residue (90%). MS 687 ($MH^+$), 704 ($MNH_4^+$), 709 ($MNa^+$).

EXAMPLE 7

Under argon 15.53 g (26 mmol) of a mixture of (1R,3'R) and (1S,3'R)-(1'-allyl-oxy-carbonyl-2-oxo-[1,3'] bipyrrolidinyl-3-yl)-triphenyl-phosphonium bromide (1:1) are dissolved in 200 ml of methylene chloride, about 5 g of sodium sulphate are added, and the suspension is stirred at room temperature for 10 min. The sodium sulphate is filtered off and the filtrate evaporated. The residue is dissolved in 40 ml of methylene chloride and 100 ml of toluene are added. The resulting red-brown solution is cooled to −70° C. At this temperature a solution of 2.69 g (24 mmol) of potassium tert.-butylate in 40 ml of THF is added dropwise within 15 min. The resulting brown solution is further stirred for 10 min, and subsequently a solution of 9.89 g (20 mmol) of diphenylmethyl (6R,7R)-7-(1-tert-butoxyformamido)-3-formyl-8-oxo-5-thia-1-azabicyclo[4.2.0]oct-2-ene-2-carboxylate in 40 ml of THF is added dropwise within 20 min. The brown solution is further stirred for about 3 hours and then brought to 0° C. After 40 min at 0° C. a solution of 6 g of citric acid in 60 ml of water and 60 ml of ethyl acetate is added within 5 min. The reaction mixture is further stirred for 10 min and then stored at about 5° C. overnight. The resulting two-phase solution is extracted, in that after equilibration the aqueous phase is further extracted with 60 ml of ethyl acetate; 60 ml of saturated sodium chloride solution is extracted with the two organic phases. The organic phases are then combined, dried and evaporated to dryness to yield 31.11 g of (E)-(6R,7R)-3-[(R)-1'-allyloxycarbonyl-2-oxo-[1,3]bipyrrolidinyl-3-ylidenemethyl]-7-tert-butoxycarbonylamino-8-oxo-5-thia-1-azabicyclo[4.2.0] oct-2-ene-carboxylic acid benzhydryl ester as a reddish-brown residue. The residue is dissolved in 20 ml of methylene chloride and with stirring poured slowly onto 180 ml of n-hexane. The resulting suspension is stirred 5 min at room temperature and then filtered. The residue according to HPLC contains a considerable amount of triphenyl-phosphine oxide (TPPO), and the above procedure is therefore repeated once and the residue dried (45° C./30 mbar/15 min) to yield 11.78 g of (E)-(6R,7R)-3-[(R) -1'-allyloxy-carbonyl-2oxo-[1,3']bipyrrolidinyl-3-ylidenemethyl]-7-tert-butoxycarbonylamino-8-oxo-5thia-1-aza-bicyclo[4.2.0]oct-2-ene-carboxylic acid benzhydryl ester as beige crystals (82%). This product according to HPLC still contains about 9.5% of triphenyl phosphine oxide (TPPO), which brings the corrected yield to 75%.

EXAMPLE 8

Under argon 75.33 g (130.0 mmol) of mixture of (1R,3'R) and (1'S,3'R)-(1'-allyl-oxy-carbonyl-2-oxo-[1,3'] bipyrrolidinyl-3-yl)-triphenyl-phosphonium bromide (1:1) are dissolved in 500 ml of methylene chloride; 20 g of sodium sulphate are added and stirred at room temperature for 15 min. The sodium sulphate is filtered off, washed well with methylene chloride and the filtrate evaporated. The residue is dissolved in 200 ml of methylene chloride, 500 ml of toluene are added and the solution cooled to −70° C. At this temperature a solution of 13.60 g (120.0 mmol) of potassium tert.-butylate in 200 ml of THF are added dropwise within 20 min. The mixture is further stirred for 20 min and a solution of 50.71 g (100 mmol) of 4-methoxybenzyl-(6R,7R)-7-phenylacetylamino-3-formyl-8-oxo-5-thia-1-azabicyclo-[4.2.0]oct-2-ene-2-carboxylate in 220 ml of THF is added dropwise within 30 min. After 2 hours at −70° C. the reaction mixture is brought to −10 C. This reaction mixture is quenched into a mixture of 400 ml of ethyl acetate and a solution of 30.02 g (156 mmol) of citric acid in 300 ml water, all previously adjusted to 0° C. The resulting two-phase mixture is brought to room temperature, the aqueous phase is separated and extracted once with 400 ml of ethyl acetate. The two organic phases are extracted once with 300 ml of saturated aqueous sodium chloride solution; the organic phases are combined, dried and evaporated to yield 256.76 g of (E)-(6R, 7R)-3[(R)-1-allyloxycarbonyl-2-oxo-[1.3']bipyrrolidinyl-3-ylidenemethyl]-8-oxo-7-phenylacetylamino-5-thia-1-azabicyclo[4.2.0]oct-2-ene-2-carboxylic acid 4-methoxybenzyl ester as a dark-brown syrup. According to HPLC this product still obtains TPPO and toluene residues. Physical characteristics:

Ms 687 ($MH^+$), 704 ($MNH_4^+$), 709 ($MNa^+$)

NMR 1.9–2.25 (m, 2H), 2.6–2.9 (m, 2H), 3.25–3.7 (m, 10H), 3.8 (s, 3H), 4.6 (d, 2H), 4.8 (q, 1H), 4.9 (d, 1H), 5.2 (s, 2H), 5.2–5.3 (m, 2H), 5.8 (dd, 1H), 5.9 (m,1H), 6.5 (m, 1H), 7.3 (m, 9H)

What is claimed is:
1. A process for producing a compound of formula

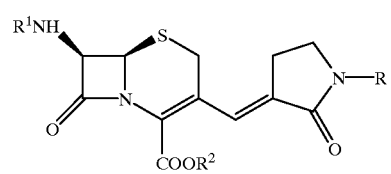

wherein
R[1] is an amino protecting group,
R[2] is a carboxy protecting group, and
R is hydrogen, lower alkyl, lower alkoxy, cycloalkyl, cycloalkenyl, cycloalkyl-lower alkyl, lower alkenyl, lower alkynyl, aryl, aryl-lower alkyl, heterocyclyl or heterocyclyl-lower alkyl; the lower alkyl, cycloalkyl, lower alkenyl, cycloalkenyl, lower alkynyl, aryl-lower alkyl, aryl and each heterocyclyl moiety being an unsaturated or saturated, 5-, 6-, or 7-membered heterocyclic ring having at least one hetero atom selected from the group consisting of oxygen, nitrogen and sulfur, and unsubstituted or substituted with at least one group selected from carboxy, amino, aminoethyl, carbamoyl, nitro, cyano, lower alkyl, lower alkoxy, hydroxy, halogen, trifluoromethyl and allyloxycarbonyl which is substituted on a ring nitrogen of pyrrolidinyl which comprises treating a phosphonium salt of formula

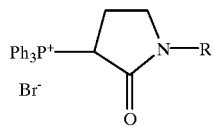

II in a toluene reaction mixture with a base, said base being present in a molar amount which is less than the molar amount of said phosphonium salt, to form an ylide of formula

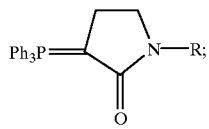

III coupling the ylide of formula III with an aldehyde of formula

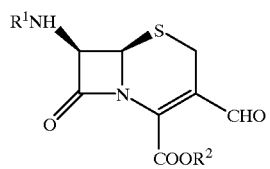

IV by adding to the reaction mixture a solution of the aldehyde of formula IV in a polar solvent at a temperature of from about −80° C. to about 0° C.; to produce the compound of formula I.

2. A process of claim 1 for producing a compound of formula

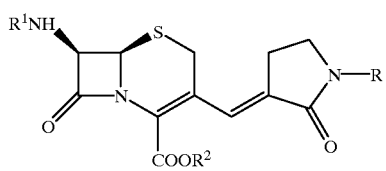

I wherein
R¹ is an amino protecting group,
R² is a carboxy protecting group, and
R is hydrogen, lower alkyl, lower alkoxy, cycloalkyl, cycloalkenyl, cycloalkyl-lower alkyl, lower alkenyl, lower alkynyl, aryl, aryl-lower alkyl, heterocyclyl or heterocyclyl-lower alkyl; the lower alkyl, cycloalkyl, lower alkenyl, cycloalkenyl, lower alkynyl, aryl-lower alkyl, aryl and each heterocyclyl moiety being an unsaturated or saturated, 5-, 6-, or 7-membered heterocyclic ring having at least one hetero atom selected from the group consisting of oxygen, nitrogen and sulfur, and unsubstituted or substituted with at least one group selected from carboxy, amino, aminoethyl, carbamoyl, nitro, cyano, lower alkyl, lower alkoxy, hydroxy, halogen, trifluoromethyl and allyloxycarbonyl which is substituted on a ring nitrogen of pyrrolidinyl which comprises treating a phosphonium salt of formula

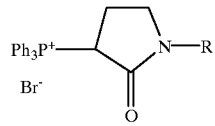

II in a toluene reaction mixture with a base to form an ylide of formula

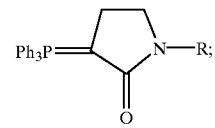

III coupling the ylide of formula III with an aldehyde of formula

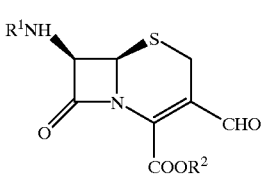

IV by adding to the reaction mixture a solution of the aldehyde of formula IV in a polar solvent at a temperature of from about −80° C. to about 0° C.;
wherein said base, ylide, and aldehyde are present in the reaction mixture during the formation of the compound of formula 1 in molar ratio of about 1.15:1.1:1.0 to 1.3:1.25:1.0, to produce the compound of formula I.

3. A process of claim 2 wherein the molar ratio is about 1.2:1.15:1.0.

4. A process of claim 2 wherein the polar solvent is tetrahydrofuran.

5. A process of claim 2 wherein the base is aqueous sodium hydroxide.

6. A process of claim 2 wherein the base is potassium tert.butoxide in tetrahydrofuran.

7. A process of claim 4 wherein the toluene reaction mixture further comprises methylene chloride.

8. A process of claim 6 wherein the toluene reaction mixture further comprises methylene chloride and the polar solvent is tetrahydrofuran.

9. A process of claim 8 wherein the weight ratio of toluene, methylene chloride, and tetrahydrofuran is between about 2:1:1 to 5:2:1.

10. A process of claim 2 wherein the coupling of the ylide of formula III with the aldehyde of formula IV is carried out at a reaction temperature between about −80° C. and about −60° C.

11. A process of claim 10 wherein the reaction temperature is about −70° C.

12. A process of claim 2 wherein the aldehyde of formula IV is diphenylmethyl (6R,7R)-7-(1-tert-butoxyformamido)-3-formyl-8-oxo-5-thia-1-azabicyclo[4.2.0]oct-2ene-2-carboxylate.

13. A process of claim 2 wherein the aldehyde of formula IV is 4-methoxybenzyl (6R,7R)-7-phenylacetylamino-3-formyl-8-oxo-5-thia-1-azabicyclo[4.2.0]oct-2-ene-2-carboxylate.

14. A process of claim 2 wherein R is 2,2,2-trifluoroethyl, cyclopropyl or cyclopropylmethyl.

15. A process of claim 2 wherein R is heterocyclyl.

16. A process of claim 15 wherein R is N-substituted 3-pyrrolidinyl.

17. A process of claim 16 wherein R is N-allyloxycarbonyl-3-pyrrolidinyl.

18. A process of claim 9 wherein R is N-substituted 3-pyrrolidinyl.

* * * * *